United States Patent
Kohno et al.

(10) Patent No.: US 11,681,137 B2
(45) Date of Patent: Jun. 20, 2023

(54) ENDOSCOPE IMAGING UNIT AND ENDOSCOPE

(71) Applicant: i-PRO Co., Ltd., Tokyo (JP)

(72) Inventors: Haruhiko Kohno, Fukuoka (JP); Naomi Shirai, Fukuoka (JP); Satoru Miyanishi, Fukuoka (JP)

(73) Assignee: I-PRO CO., LTD., Tokyo (JP)

( * ) Notice: Subject to any disclaimer, the term of this patent is extended or adjusted under 35 U.S.C. 154(b) by 544 days.

(21) Appl. No.: 16/514,185

(22) Filed: Jul. 17, 2019

(65) Prior Publication Data
US 2020/0022571 A1    Jan. 23, 2020

(30) Foreign Application Priority Data

Jul. 18, 2018  (JP) .............................. JP2018-135094

(51) Int. Cl.
*G02B 23/24* (2006.01)
*A61B 1/05* (2006.01)
(Continued)

(52) U.S. Cl.
CPC ...... *G02B 23/2461* (2013.01); *A61B 1/00009* (2013.01); *A61B 1/05* (2013.01); *A61B 1/0676* (2013.01); *G02B 23/2415* (2013.01)

(58) Field of Classification Search
CPC ............ A61B 1/00009; A61B 1/00124; A61B 1/00128; A61B 1/00193; A61B 1/051;
(Continued)

(56) References Cited

U.S. PATENT DOCUMENTS 5,220,198 A * 6/1993 Tsuji ........................ A61B 1/05
257/680
5,454,366 A * 10/1995 Ito .......................... A61B 1/051
348/E5.025
(Continued)

FOREIGN PATENT DOCUMENTS

JP    H06178757 A  *  6/1994
JP     6-233196 A       8/1994
(Continued)

OTHER PUBLICATIONS

Japanese Office Action, dated Jan. 18, 2022, for Japanese Application No. 2018-135094. (7 pages), (with English translation).

*Primary Examiner* — Aaron B Fairchild
*Assistant Examiner* — Julianna J Nicolaus
(74) *Attorney, Agent, or Firm* — Seed IP Law Group LLP

(57) ABSTRACT

There is provided an endoscope imaging unit including parallel electric wires, an image sensor located on a front end side by being separated from front ends of the respective electric wires, and having a light incident surface substantially perpendicular to the electric wires, a flexible substrate located between the electric wires and the image sensor, having a circuit, and conductively connecting the respective electric wires to the circuit, an image sensor mounting peninsula portion bent with respect to the substrate, and mounting the image sensor thereon by conductively connecting the image sensor to the circuit, and a circuit mounting peninsula portion extending from the substrate, located by being bent to a side opposite to the image sensor before the image sensor mounting peninsula portion, and mounting and conductively connecting an electronic component or the circuit pattern to the circuit.

13 Claims, 11 Drawing Sheets

(51) Int. Cl.
*A61B 1/06* (2006.01)
*A61B 1/00* (2006.01)

(58) Field of Classification Search
CPC .... A61B 1/0676; A61B 1/05; G02B 23/2415; G02B 23/2423; G02B 23/2461
See application file for complete search history.

(56) References Cited

U.S. PATENT DOCUMENTS

| | | | |
|---|---|---|---|
| 6,313,456 B1 | 11/2001 | Miyashita et al. | |
| 2002/0080233 A1* | 6/2002 | Irion | H04N 5/2253 348/E5.025 |
| 2009/0268019 A1 | 10/2009 | Ishii et al. | |
| 2010/0185052 A1* | 7/2010 | Chang | H04N 5/2253 600/112 |
| 2013/0169777 A1* | 7/2013 | Zen | A61B 1/051 348/76 |
| 2014/0078280 A1* | 3/2014 | Yoshida | A61B 1/00163 348/76 |
| 2015/0358518 A1 | 12/2015 | Ishii et al. | |
| 2015/0378144 A1 | 12/2015 | Handte et al. | |
| 2016/0338579 A1 | 11/2016 | Amano | |
| 2017/0108691 A1* | 4/2017 | Kitano | H04N 5/2256 |
| 2017/0251913 A1* | 9/2017 | Birnkrant | H05K 1/189 |
| 2018/0049628 A1* | 2/2018 | Motohara | H01L 27/14 |
| 2018/0070803 A1* | 3/2018 | Mikami | A61B 1/00163 |
| 2018/0070805 A1 | 3/2018 | Kawayoke | |
| 2018/0338674 A1* | 11/2018 | Kojima | H04N 5/2254 |
| 2019/0068848 A1* | 2/2019 | Usuda | H04N 5/335 |
| 2019/0296537 A1* | 9/2019 | Mikami | H01R 43/28 |
| 2019/0328217 A1* | 10/2019 | Moreau | A61B 1/00009 |

FOREIGN PATENT DOCUMENTS

| | | | |
|---|---|---|---|
| JP | 10-099267 A | | 4/1998 |
| JP | 2000-210252 A | | 8/2000 |
| JP | 2008-177701 A | | 7/2008 |
| JP | 2008-237732 A | | 10/2008 |
| JP | 2009-039433 A | | 2/2009 |
| JP | 2014087705 A | * | 5/2014 |
| JP | 2016-214660 A | | 12/2016 |
| JP | 2017-094098 A | | 6/2017 |
| WO | 2012/077116 A1 | | 6/2012 |
| WO | 2016/189679 A1 | | 12/2016 |

\* cited by examiner

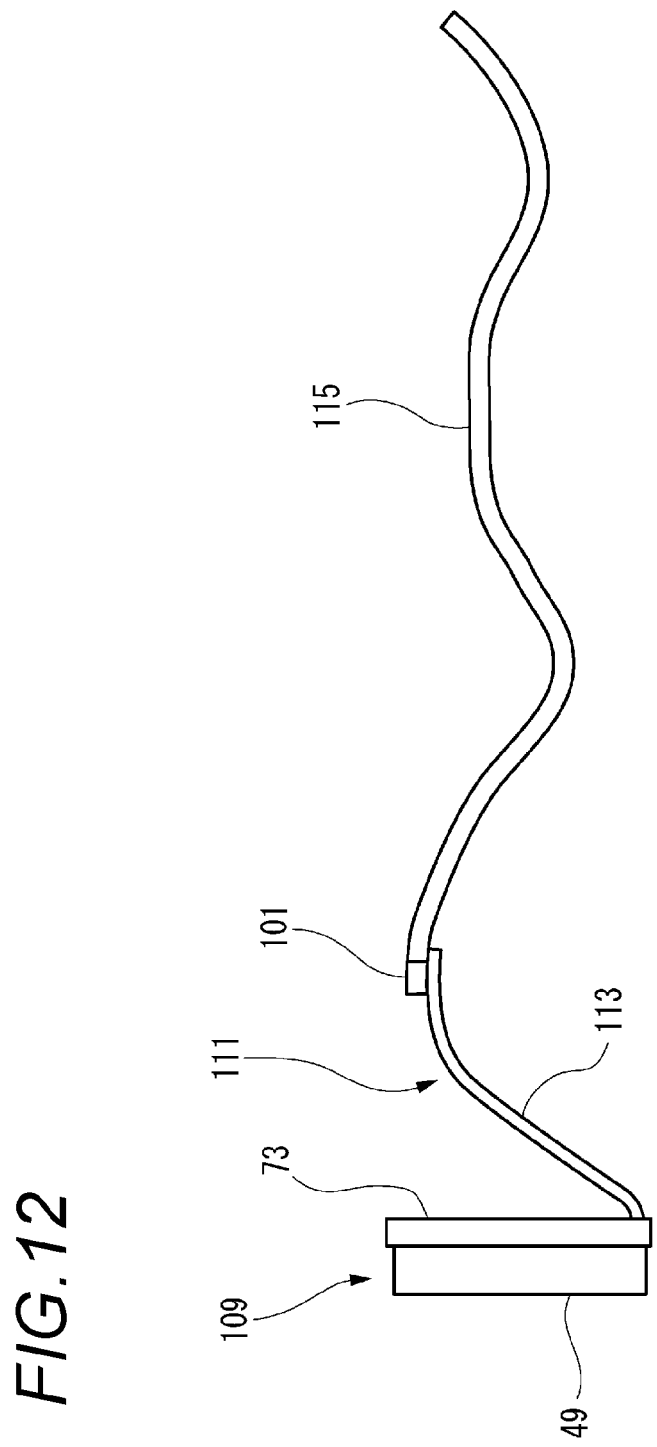

ENDOSCOPE IMAGING UNIT AND ENDOSCOPE

BACKGROUND OF THE INVENTION

1. Field of the Invention

The present disclosure relates to an endoscope imaging unit and an endoscope.

2. Description of the Related Art

JP-A-2008-237732 as Patent Reference 1 discloses an imaging device including an image sensor linked to an objective optical system, a circuit substrate connected to the image sensor and having an electronic component and a signal line connection terminal, and a signal line connected to the circuit substrate within a projection area range of the image sensor. In the imaging device, the circuit substrate has at least a first surface extending rearward from the image sensor, and a second surface and a third surface which are bent so as to be inclined at a predetermined angle with reference to the first surface. The imaging device is formed in a cylindrical shape having a polygonal cross section by using the plurality of surfaces. Edge portions brought into close contact with each other so as to match the circuit substrate are fixed to each other by a fixing tool. An electrical circuit of the circuit substrate is formed in such a way that electric connection portions disposed in respective end portions of the edge portions of the circuit substrate are electrically connected to each other by the fixing tool.

Patent Reference 1: JP-A-2008-237732

SUMMARY OF THE INVENTION

However, according to the configuration disclosed in JP-A-2008-237732, the electronic component and the signal line connection terminal are mixed and disposed on an inner surface and an outer surface of the circuit substrate formed in the cylindrical shape. Therefore, the electronic component that requires a three-dimensional space in a height direction from a mounting surface at the time of mounting and the signal line connection terminals that require a long insulation distance between each other are not arranged at proper positions in a proper manner. Consequently, an outer diameter of an endoscope is less likely to be reduced.

The present disclosure is devised in view of the above-described circumstances in the related art, and aims to provide an endoscope imaging unit and an endoscope in which an outer shape or a volume can be minimized by obtaining a connection structure suitable for an electric wire and an electronic component within a projection area range of an image sensor when viewed from a front end side, and in which an outer diameter can be reduced.

According to the present disclosure, there is provided an endoscope imaging unit including a plurality of parallel electric wires insulated from each other, an image sensor located on a front end side by being separated from a front end of the respective electric wires, wherein the image sensor has a light incident surface substantially perpendicular to the electric wires and facing the front end side, a flexible substrate located between the electric wires and the image sensor, having a circuit, and conductively connecting the respective electric wires to the circuit, an image sensor mounting peninsula portion bent with respect to the flexible substrate, and mounting the image sensor thereon by conductively connecting the image sensor to the circuit, and a circuit mounting peninsula portion extending from the flexible substrate, located by being bent to a side opposite to the image sensor before the image sensor mounting peninsula portion, and mounting an electronic component or a circuit pattern by conductively connecting the electronic component or the circuit pattern.

In addition, according to the present disclosure, there is provided an endoscope including a plurality of parallel electric wires insulated from each other, an image sensor located on a front end side by being separated from a front end of the respective electric wires, wherein the image sensor has a light incident surface substantially perpendicular to the electric wires and facing the front end side, a flexible substrate located between the electric wires and the image sensor, having a circuit, and conductively connecting the respective electric wires to the circuit, an image sensor mounting peninsula portion bent with respect to the flexible substrate, and mounting the image sensor thereon by conductively connecting the image sensor to the circuit, a circuit mounting peninsula portion extending from the flexible substrate, located by being bent to a side opposite to the image sensor before the image sensor mounting peninsula portion, and mounting an electronic component or a circuit pattern by conductively connecting the electronic component or the circuit pattern, and an optical unit that causes light reflected from an object to form an image on the light incident surface.

According to the present disclosure, in the endoscope imaging unit or the endoscope, an outer shape or a volume can be minimized by obtaining a connection structure suitable for the electric wire and the electronic component within the projection area range of an image sensor when viewed from the front end side, and furthermore, the outer diameter of the endoscope can be reduced.

BRIEF DESCRIPTION OF THE DRAWINGS

In the accompanying drawings:

FIG. 12 is a side view of the endoscope imaging unit illustrated in FIG. 11.

DETAILED DESCRIPTION OF THE EXEMPLARY EMBODIMENTS

Hereinafter, embodiments specifically disclosing an endoscope imaging unit and an endoscope according to the present disclosure will be described in detail with reference to the drawings as appropriate. Unnecessarily detailed description may be omitted in some cases. For example, detailed description of well-known items or repeated description of substantially the same configuration may be omitted in some cases. The reason is to avoid the following description from being unnecessarily redundant, and to facilitate understanding of those skilled in the art. The accompanying drawings and the following description are provided in order to enable those skilled in the art to fully understand the present disclosure, and are not intended to limit a gist disclosed in the appended claims.

Embodiment 1

Figure 1:
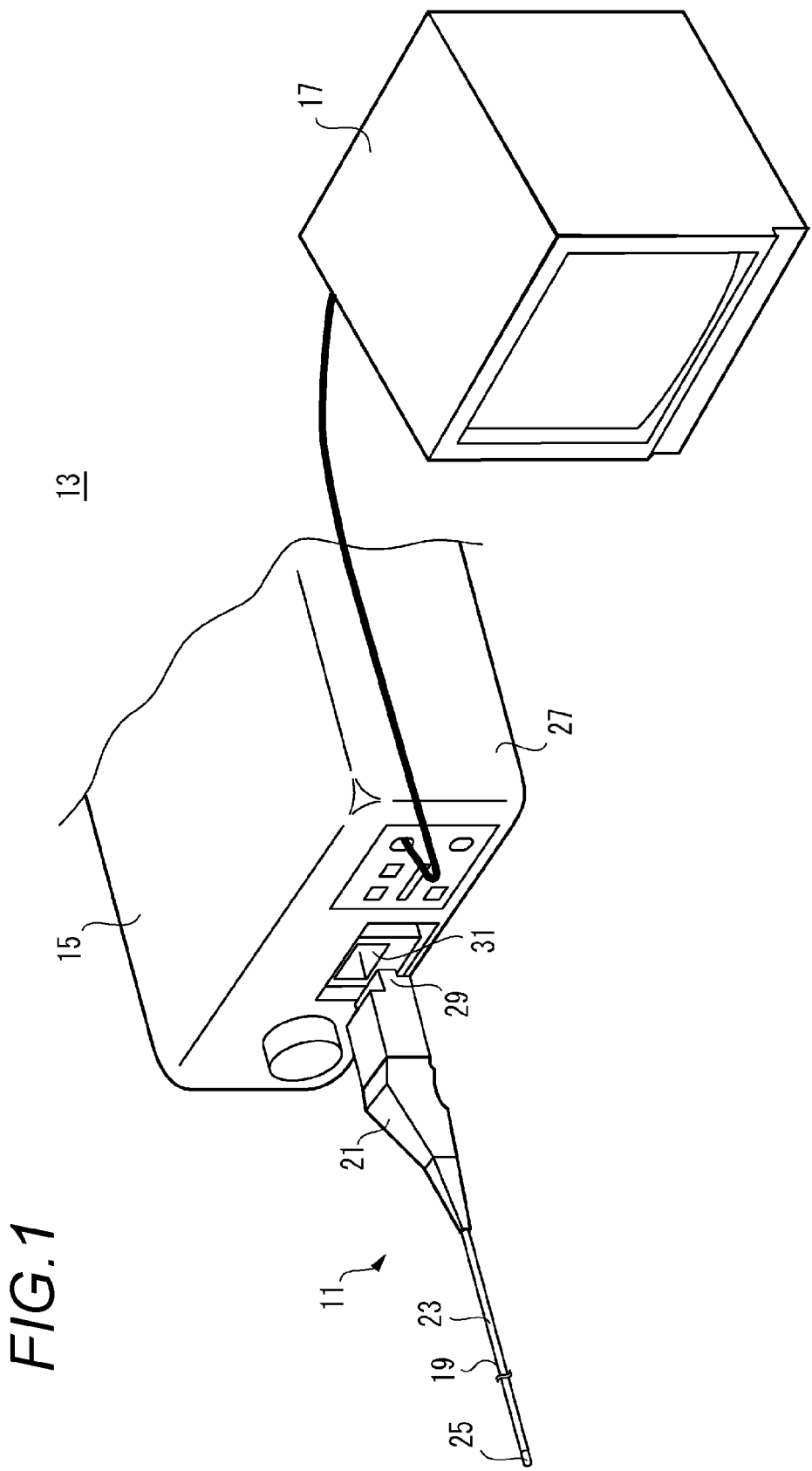
FIG. 1 is a perspective view illustrating an exterior example of an endoscope system including an endoscope according to Embodiment 1.

FIG. 1 is a perspective view illustrating an exterior example of an endoscope system 13 including an endoscope 11 according to Embodiment 1. The endoscope system 13 includes the endoscope 11, a video processor 15, and a monitor 17. For example, the endoscope 11 is a flexible endoscope for a medical use. The video processor 15 performs image processing on a captured image (including a still image and a moving image) obtained by the endoscope 11 imaging an observation target (here, a surface or a body interior of a human body serving as a test object). The monitor 17 displays the captured image output from the video processor 15. For example, the image processing includes tone correction, gray level correction, and gain adjustment.

The endoscope 11 images the observation target (for example, the surface or the body interior of the human body serving as the test object). The endoscope 11 includes a scope 19 inserted into the observation target and a plug portion 21 to which a rear end portion of the scope 19 is connected. In addition, the scope 19 is configured to include a relatively long and flexible soft portion 23 and a rigid hard portion 25 disposed in a front end of the soft portion 23.

The video processor 15 has a housing 27, performs the image processing on the image captured by the endoscope 11, and outputs the captured image subjected to the image processing to the monitor 17. A front surface of the housing 27 has a socket portion 31 into which a proximal end portion 29 of a plug portion 21 is inserted. The plug portion 21 is inserted into the socket portion 31, and the endoscope 11 and the video processor 15 are connected to each other. In this manner, power and various signals (for example, a video signal and a control signal) can be transmitted and received between the endoscope 11 and the video processor 15. The power and various signals are introduced from the plug portion 21 to the soft portion 23 via a transmission cable (a bundle of electric wires 69 to be described later) inserted into the scope 19. In addition, a signal of the captured image output from an image sensor (that is, an image element) disposed inside the hard portion 25 is transmitted from the plug portion 21 to the video processor 15 via the transmission cable. In addition, the soft portion 23 is movable (for example, bent) in response to an input operation to an operation unit (not illustrated) of the endoscope 11.

The video processor 15 performs the image processing on the signal of the captured image transmitted via the transmission cable, converts the captured image subjected to the image processing into a display signal, and outputs the display signal to the monitor 17.

For example, the monitor 17 is configured to employ a display device such as a liquid crystal display (LCD) or a cathode ray tube (CRT). The monitor 17 according to Embodiment 1 can display an image of an object imaged by the endoscope 11 in a three-dimensional method.

Figure 2:
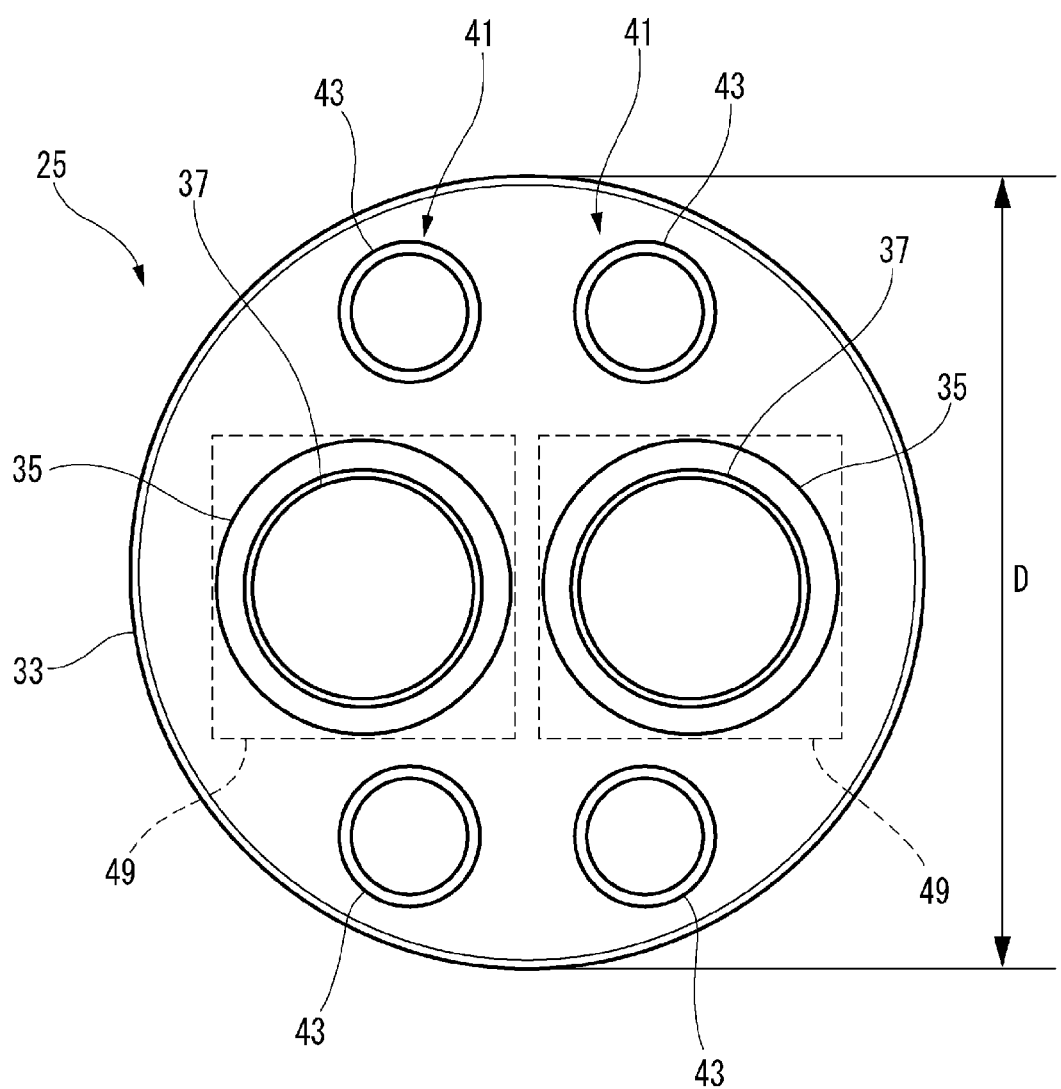
FIG. 2 is a front view of the endoscope illustrated in FIG. 1.

FIG. 2 is a front view of the endoscope 11 illustrated in FIG. 1. A front end of the hard portion 25 has a circular front end flange 33 made of a metal material such as SUS. In the endoscope 11, an outer diameter D of the front end flange 33 is a maximum outer diameter. A pair of imaging windows 35 is arranged laterally symmetrically on a front end surface of the front end flange 33. For example, the imaging window 35 is formed by including an optical material such as an optical glass or an optical plastic, and receives light from the surface or the body interior of the test object into which the front end side of the endoscope 11 is inserted. According to Embodiment 1, for example, the imaging window 35 is configured to have a cover glass 37.

In the endoscope 11, each rear surface portion of the pair of imaging windows 35 is provided with an optical unit 39 (refer to FIG. 3) to be described later. The endoscope 11 has the pair of imaging windows 35, thereby enabling 3D imaging to be performed on the surface or the body interior of the test object. For example, a 3D display method includes a parallax information method. According to the parallax information method, the captured image including parallax information obtained by the pair of imaging windows 35 and the optical unit 39 is combined into one image signal, and is displayed on the monitor 17. The image displayed on the monitor 17 is a parallax image captured from two points of view. In this case, information possessed by each image is the same as a normal 2D image. An observer views the combined image, thereby enabling the observer to visually recognize the combined image as a 3D image. The 3D display method is not limited to the above-described parallax information method. Alternatively, the 3D display method may be a method (depth reproduction method) in which a depth position is added to pixel information of each two-dimensional pixel so as to obtain stereoscopic information.

The endoscope 11 includes an illumination unit 41 that emits illumination light to the object. In the endoscope 11, two pairs of emitting windows 43 are laterally arranged across the respective imaging windows 35 on a front end surface of the front end flange 33. For example, in the pair of emitting window 43 across the respective imaging windows 35, one is the emitting window for IR excitation light, and the other is the emitting window for white light.

Figure 3:
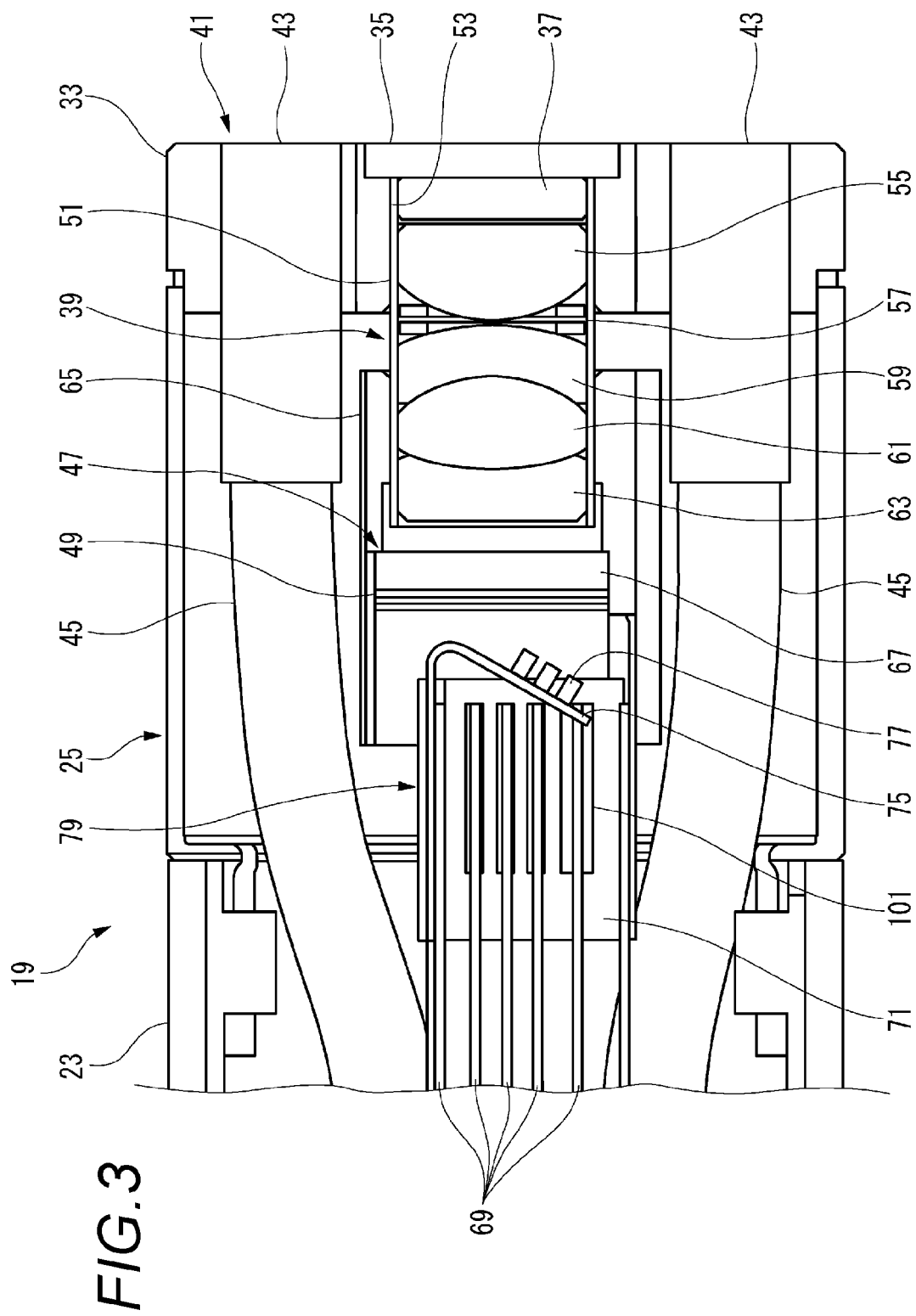
FIG. 3 is a side perspective view of FIG. 2.

FIG. 3 is a side perspective view of FIG. 2. The side perspective view of FIG. 3 illustrates a state where an interior of the scope 19 is perspectively viewed from a right side surface, based on a viewing direction of the scope 19 of the front end from a proximal end side of the endoscope 11 illustrated in FIG. 1. A state where the interior of the scope 19 is perspectively viewed from a left side surface is omitted in the illustration. The hard portion 25 of the endoscope 11 includes the pair of (that is, two) optical units 39 corresponding to the respective imaging windows 35. In the hard portion 25, each of the optical units 39 is located between a pair of optical fibers 45 connected to each of the pair of emitting windows 43. For example, the optical fiber 45 can employ a single optical fiber wire. In addition, as the optical fiber 45, a bundle fiber may be used in which a plurality of optical fiber wires are bundled.

The pair of optical units 39 has substantially the same configuration. The optical unit 39 forms an image of the light transmitted from the imaging window 35 on the light incident surface of the image sensor 49 in the endoscope imaging unit 47 disposed in a rear stage. The optical unit 39 has a cylindrical optical column 51 for housing a plurality of optical components. In the optical column 51, a front end outer periphery thereof is fixed to an inner periphery 53 of the front end flange 33, and a rear end thereof protrudes rearward from the front end flange 33.

The optical column 51 internally houses the above-described cover glass 37, a first lens 55, a spacer 57, a second lens 59, a third lens 61, and a fourth lens 63 in order from the front end side. The spacer 57 is interposed between the first lens 55 and the second lens 59, and stably holds the first lens 55 and the second lens 59 while preventing contact between both convex surfaces. A rear holder 65 is fitted to a rear outer periphery of the optical column 51. The rear holder 65 holds the image sensor 49 in the rear end. A sensor cover glass 67 is fixed to the light incident surface side of the image sensor 49. The image sensor 49 is fixed to the rear holder 65 via the sensor cover glass 67. In the image sensor 49, the inner periphery of the rear holder 65 is fitted to the outer periphery of the optical column 51. In this manner, the center of the light incident surface is positioned in the center of the optical unit 39.

In the endoscope 11 according to Embodiment 1, each rear portion of the optical unit 39 includes the endoscope imaging unit 47 according to Embodiment 1. As a main configuration, the endoscope imaging unit 47 has the electric wires 69, the image sensor 49, a flexible substrate 71, an image sensor mounting peninsula portion 73, an electronic component mounting peninsula portion 75, and an electronic component 77.

The plurality of electric wires 69 are insulated from each other, and are arranged in parallel. The plurality of electric wires 69 are bundled and covered by a sheath so as to serve as the above-described transmission cable described above, and are inserted into the soft portion 23. According to Embodiment 1, a core wire of the electric wire 69 serves as a round conductor having a round cross section, and an outer periphery thereof is insulated. The outer periphery of the electric wire 69 may be further covered by a shield conductor.

The image sensor 49 is located forward (that is, on the front end side of the endoscope 11) by being separated from the front end of the electric wire 69. In the image sensor 49, the light incident surface substantially perpendicular to the front end straight portion of the electric wire 69 faces forward. That is, in the image sensor 49, the light incident surface of the image sensor 49 is located to face the fourth lens 63 of the optical unit 39 via the sensor cover glass 67. For example, as the image sensor 49, a charge coupled device (CCD) or a complementary metal oxide semiconductor (CMOS) is used.

The flexible substrate 71 serving as an example of the substrate is located between the electric wire 69 and the image sensor 49. The flexible substrate 71 has a circuit on which a plurality of linear conductors are subjected to pattern printing. In the flexible substrate 71, the respective electric wires 69 are conductively connected to the circuit. The flexible substrate 71 is flexible. The flexible substrate 71 is located within the projection area range of the image sensor 49 in a direction in which the proximal end side is viewed from the front end side (for example, the hard portion 25 or the soft portion 23) of the endoscope 11. In other words, when the proximal end side is viewed from the front end side (for example, the hard portion 25 or the soft portion 23) of the endoscope 11, the flexible substrate 71 is located so as not protrude outward of the outer shape of the image sensor 49. As the flexible substrate 71, it is possible to use a flexible flat cable (FFC) formed into a belt-shaped flexible cable by covering a conductor made of a plurality of belt-shaped thin plates with an insulation sheet material or a flexible printed circuit board (FPC) in which a linear conductor is subjected to pattern printing on a flexible insulation substrate.

Figure 4:
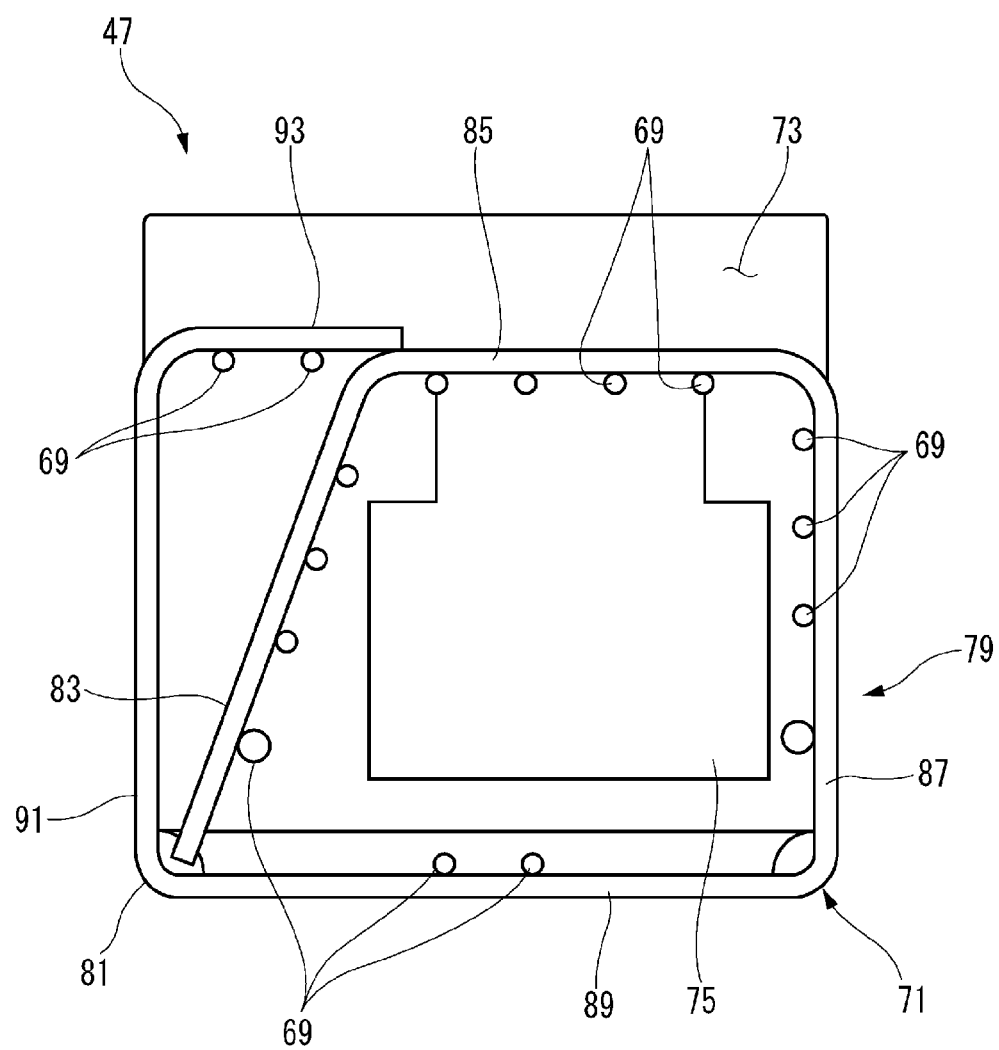
FIG. 4 is a rear view of an endoscope imaging unit illustrated in FIG. 3.

FIG. 4 is a rear view of the endoscope imaging unit 47 illustrated in FIG. 3. In the following description, upward, downward, rightward, leftward, forward, and rearward directions are set based on FIG. 4. That is, upper and lower sides of the endoscope imaging unit 47 are upper and lower sides in FIG. 4, and right and left sides of the endoscope imaging unit 47 are right and left sides in FIG. 4. In addition, a front side of the endoscope imaging unit 47 is a rear surface of the drawing in FIG. 4, and a rear side is a front surface of the drawing in FIG. 4.

In Embodiment 1, the flexible substrate 71 is bent into the tubular body 79 extending in the same direction as that of the front end straight portion of the electric wire 69. For example, the tubular body 79 can be a square tube. In the square tube, so far as the outer shape of the cross section perpendicular to the forward and rearward direction is a quadrangular, a portion of the flexible substrate 71 may be bent inward.

The flexible substrate 71 is roughly divided into a substrate main body 81, the image sensor mounting peninsula portion 73, and the electronic component mounting peninsula portion 75, and all of these are integrally molded. The substrate main body 81 is further divided into a first surface 83, a second surface 85, a third surface 87, a fourth surface 89, a fifth surface 91, and a sixth surface 93. In the tubular body 79, the first surface 83 is folded inward, and a quadrangular outer peripheral surface is configured to include the second surface 85, the third surface 87, the fourth surface 89, the fifth surface 91, and the sixth surface 93. In the flexible substrate 71, the tubular body 79 is located within the projection area range of the image sensor 49.

Figure 5:
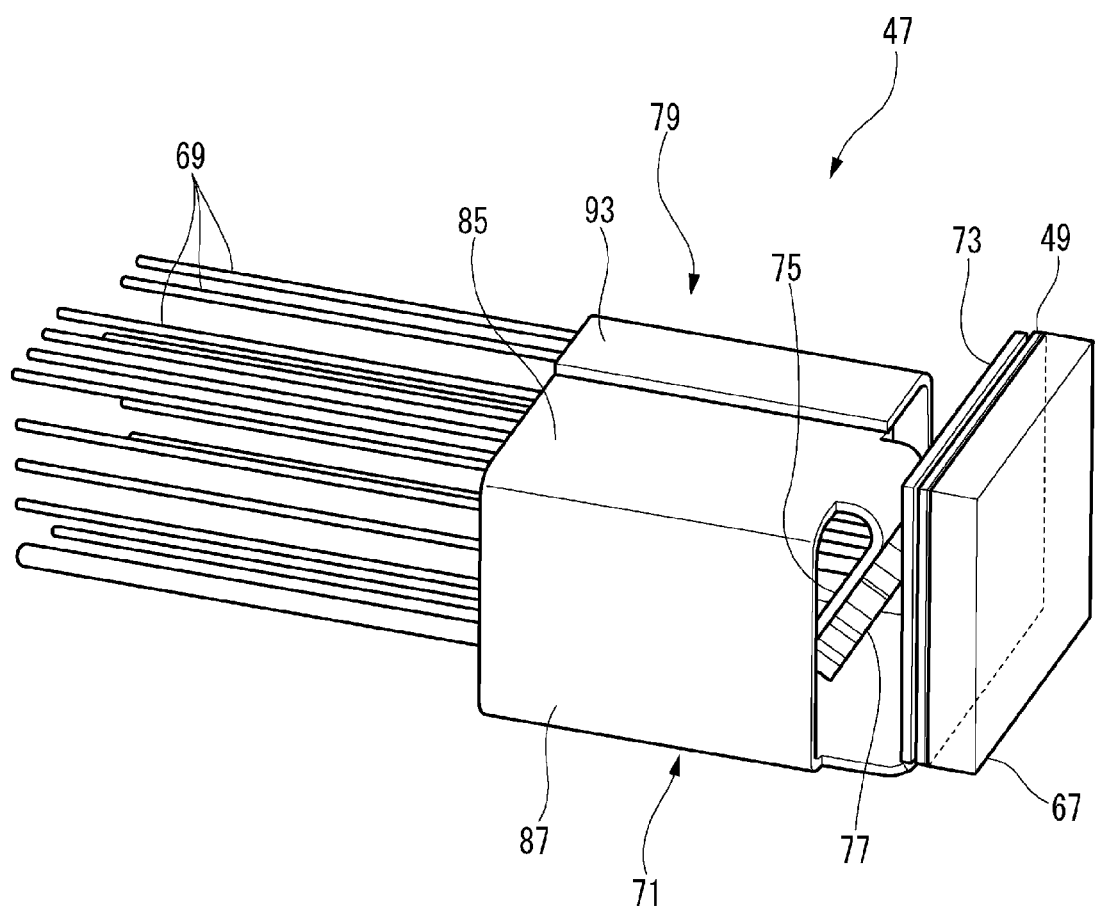
FIG. 5 is a perspective view of the endoscope imaging unit illustrated in FIG. 4.

FIG. 5 is a perspective view of the endoscope imaging unit 47 illustrated in FIG. 4. The image sensor mounting peninsula portion 73 is formed in a quadrangular shape, extends from the fourth surface 89 of the flexible substrate 71 via a constricted portion 95 (refer to FIG. 8), and mounts the image sensor 49 thereon. After the image sensor 49 is mounted on the image sensor mounting peninsula portion 73, the image sensor mounting peninsula portion 73 is bent with respect to the fourth surface 89 of the flexible substrate 71. That is, before the image sensor mounting peninsula portion 73 is bent with respect to the fourth surface 89 of the flexible substrate 71, the image sensor 49 is mounted on the image sensor mounting peninsula portion 73. The image sensor 49 is conductively connected to the circuit formed in the flexible substrate 71, and is mounted on the front surface of the image sensor mounting peninsula portion 73 bent vertically to the extension line of the tubular body 79.

Figure 6:
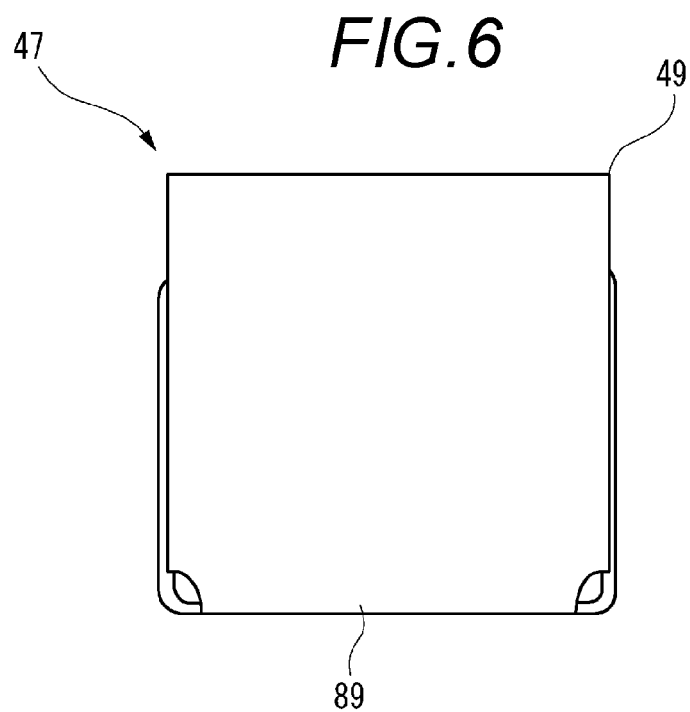
FIG. 6 is a front view of the endoscope imaging unit illustrated in FIG. 5.

FIG. 6 is a front view of the endoscope imaging unit 47 illustrated in FIG. 5. In a front view where the image sensor 49 mounted on the image sensor mounting peninsula portion 73 is viewed from the front (that is, the front end side of the endoscope 11 described above), the image sensor mounting peninsula portion 73, the tubular body 79, and the electric wire 69 are almost hidden by the rear portion of the image sensor 49. That is, in the endoscope imaging unit 47, the configuration members are stored so as not to protrude outward of the outer shape of the image sensor 49.

Figure 7:
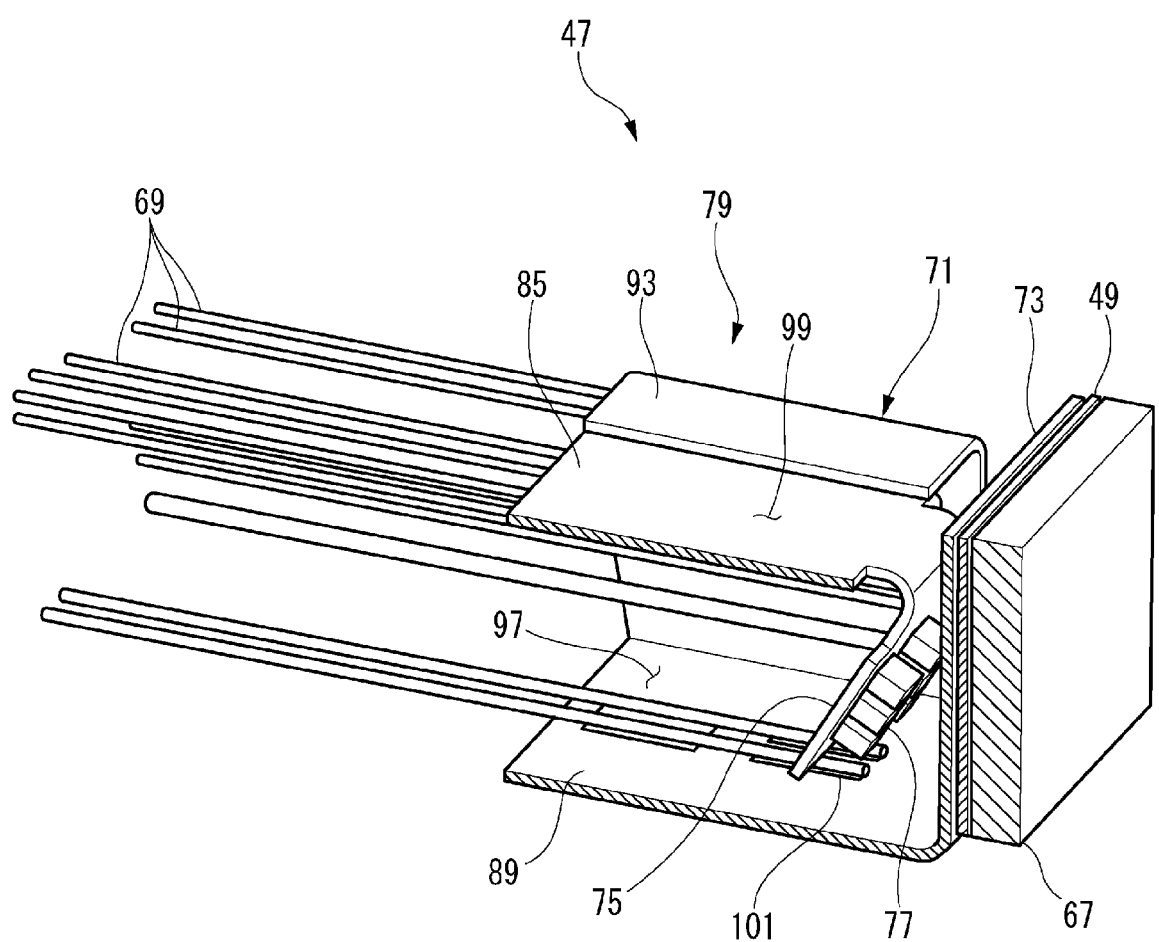
FIG. 7 is a perspective view illustrating a side portion cut out from the endoscope imaging unit illustrated in FIG. 5.

FIG. 7 is a perspective view illustrating a side portion cut out from the endoscope imaging unit 47 illustrated in FIG. 5. The electronic component mounting peninsula portion 75 (example of the circuit mounting peninsula portion) is formed in a quadrangular shape, extends from the second surface 85 of the flexible substrate 71 via the constricted portion 95 (refer to FIG. 8), and is bent to a side opposite to the image sensor 49 before the image sensor mounting peninsula portion 73. In this manner, the electronic component mounting peninsula portion 75 is located within the projection area range of the image sensor 49 in a front view when viewed from the front (that is, the front end side of the endoscope 11 described above). The plurality of electronic components 77 are conductively connected to the circuit, and are mounted on the surface where the electronic component mounting peninsula portion 75 faces the image sensor mounting peninsula portion 73. The electronic component mounting peninsula portion 75 is formed to have a size that does not bring the electronic component mounting peninsula portion 75 into contact with the inner surface 97 of the tubular body 79. The electronic component mounting peninsula portion 75 is bent at a bending angle of 90 degrees or larger so as to be reliably inserted into the tubular body 79. In this manner, interference with the image sensor mounting peninsula portion 73 is avoided.

In the electronic component mounting peninsula portion 75, the electronic component 77 may be mounted on a surface opposite to that according to Embodiment 1. In addition, a plurality of electronic component mounting peninsula portions 75 may be formed. In this case, the plurality of the electronic component mounting peninsula portions 75 are stacked on the rear surface side of the image sensor mounting peninsula portions 73, and are arranged face to face in a stacked layer shape. The electronic component mounting peninsula portion 75 may not have the electronic component such as a capacitor mounted thereon, and may only have a circuit pattern for conductive connection to the circuit formed in the flexible substrate 71.

Furthermore, in a case where the maximum outer diameter of the required endoscope has some margin, the flexible substrate 71 and the electronic component mounting peninsula portion 75 may not necessarily be arranged within the projection area range of the image sensor 49 in a front view when viewed from the front (that is, the front end side of the endoscope 11 described above). Alternatively, both of these may be located so as to slightly protrude from the projection area range of the image sensor 49 in a front view when viewed from the front to such an extent that interference with other members is minimized. In addition, in the present specification, in order to suppress an increase in the outer diameter of the endoscope 11, if the electric wire 69 and the electronic component mounting peninsula portion 75 are located to fit within the projection area range of the image sensor mounting peninsula portion 73 on which the image sensor 49 is mounted in a front view when viewed from the front (that is, the front end side of the endoscope 11 described above), the flexible substrate 71 may be located so as to partially protrude from the projection area range of the image sensor mounting peninsula portion 73 (refer to FIG. 4).

The respective electric wires 69 are conductively connected to the circuit on the inner surface 97 of the tubular body 79. The electric wires 69 are all connected to the inner surface 97 of the tubular body 79, and are not connected to an outer surface 99 of the tubular body 79.

In this way, in the endoscope imaging unit 47, the image sensor mounting peninsula portion 73 extends from the peripheral edge portion of the tubular body front end, and is bent in a direction substantially perpendicularly. The electronic component mounting peninsula portion 75 is bent by extending from the other peripheral edge portion of the tubular body front end, and is inserted into the tubular body 79.

In the endoscope imaging unit 47, the plurality of electric wires 69 are inserted into the tubular body rear end on a side opposite to the image sensor 49 (in other words, withdrawn from the tubular body rear end), and are conductively connected to the circuit via a pad 101 disposed on the inner surface 97 of the tubular body 79.

Figure 8:
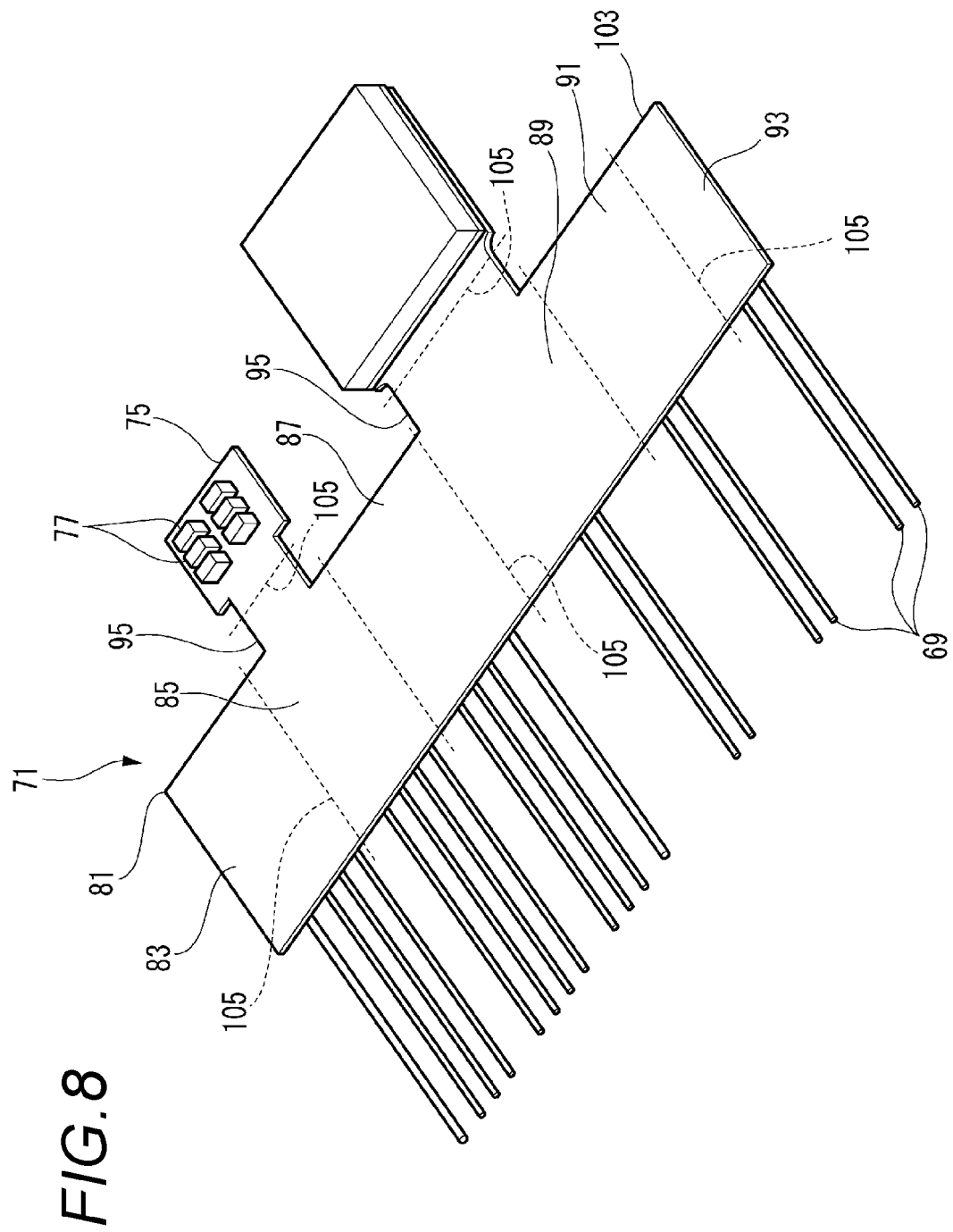
FIG. 8 is a perspective view illustrating a state where a flexible substrate of a tubular body illustrated in FIG. 5 is spread in a flat plate shape.

FIG. 8 is a perspective view illustrating a state where the flexible substrate 71 of the tubular body 79 illustrated in FIG. 5 is spread in a flat plate shape. In a state where the flexible substrate 71 is spread in the flat plate shape, the substrate main body 81 comes to have a rectangular shape. In FIG. 8, a surface serving as the outer surface 99 (refer to FIG. 7) of the tubular body 79 is drawn. In the substrate main body 81, one long side becomes an edge 103 where the peripheral edge portion of the tubular body front end is formed. In the flexible substrate 71, the electronic component mounting peninsula portion 75 extends from the edge 103 of the second surface 85 of the substrate main body 81 via the constricted portion 95. In addition, in the flexible substrate 71, the image sensor mounting peninsula portion 73 extends from the edge 103 of the fourth surface 89 of the substrate main body 81 via the constricted portion 95. In the flexible substrate 71, a fold 105 is set in a boundary among the first surface 83, the second surface 85, the third surface 87, the fourth surface 89, the fifth surface 91, the sixth surface 93, and the constricted portion 95.

Figure 9:
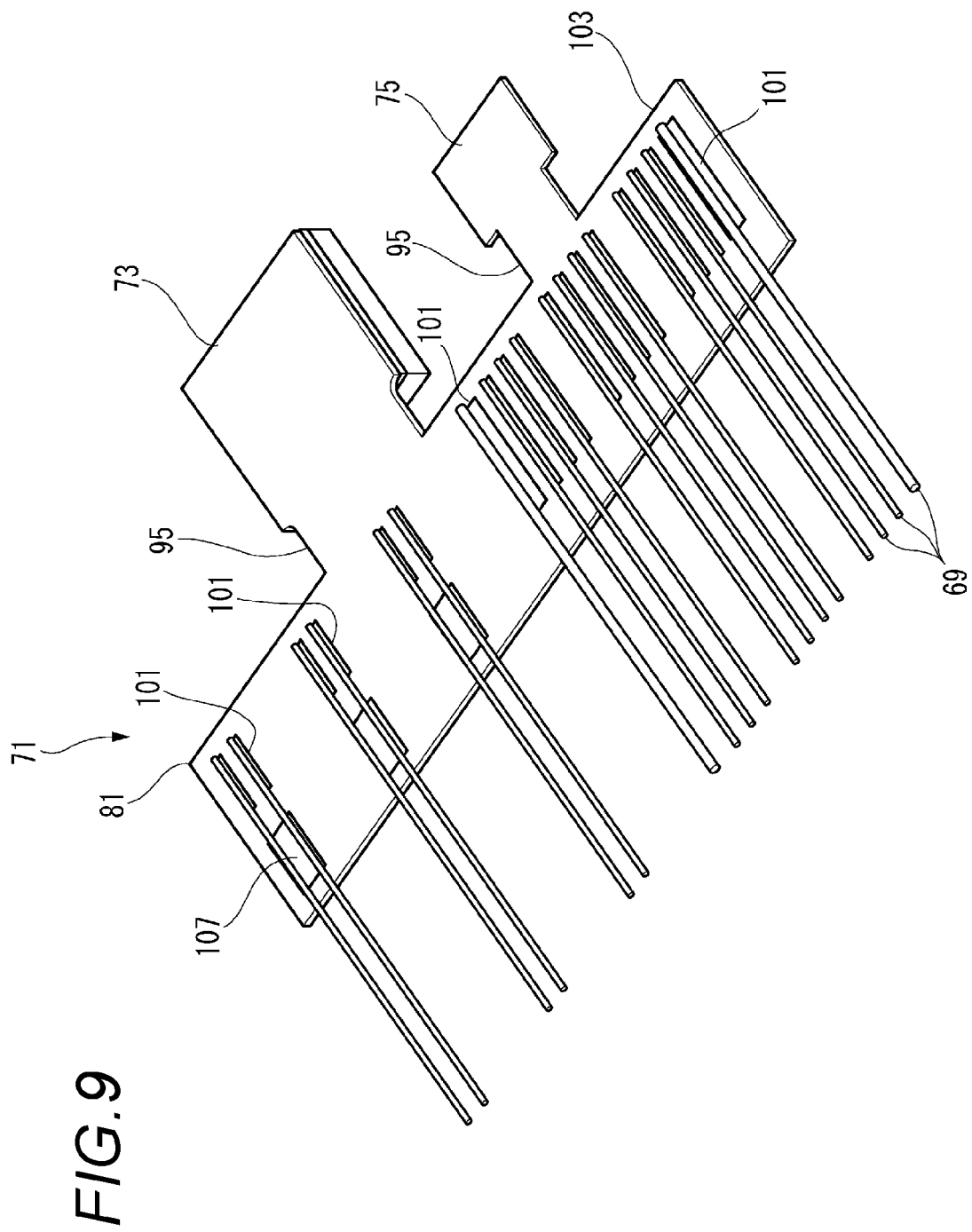
FIG. 9 is a rear view of the spread flexible substrate illustrated in FIG. 8.

FIG. 9 is a rear view of the spread flexible substrate 71 illustrated in FIG. 8. In the flexible substrate 71, the substrate main body 81 serving as the inner surface 97 (refer to FIG. 7) of the tubular body 79 has the pad 101 for conductively connecting the plurality of electric wires 69 to the circuit. In Embodiment 1, for example, 18 electric wires 69 are connected to the flexible substrate 71. As the pad 101, four are disposed on the first surface 83, four are disposed on the second surface 85, four are disposed on the third surface 87, two are disposed on the fourth surface 89, two are disposed on the fifth surface 91, and two are disposed on the sixth surface 93. In addition, in the flexible substrate 71, in a case where the electric wire 69 is a shield electric wire, a grounding pad 107 may be disposed so as to conductively connect a shield conductor covering the outer periphery to a GND circuit.

Next, an operation of the endoscope imaging unit 47 according to Embodiment 1 will be described.

The endoscope imaging unit 47 according to Embodiment 1 has the plurality of parallel electric wires 69 insulated from each other. The endoscope imaging unit 47 has the image sensor 49 which is located forward (that is, the front end of the endoscope 11 described above) by being separated from the front end of the respective electric wires 69, and the image sensor 49 has the light incident surface substantially perpendicular to the front end straight portion of the electric wire 69 and facing forward (that is, the front end side of the endoscope 11 described above). The endoscope imaging unit 47 has the flexible substrate 71 located between the electric wires 69 and the image sensor 49, having a circuit for transmitting the captured image and transmitting a control signal, and conductively connecting the respective electric wires 69 to the circuit. It is preferable that the flexible substrate 71 is located within the projection area range of the image sensor 49 in a front view when viewed from the front (that is, the front end of the endoscope 11 described above). However, the flexible substrate 71 may be located so that a portion of the flexible substrate 71 slightly protrudes to such an extent that interference with other members is minimized. The endoscope imaging unit 47 has the image sensor mounting peninsula portion 73 which is bent with respect to the fourth surface 89 of the flexible substrate 71, which conductively connects the image sensor 49 to the circuit, and which mounts the image sensor 49 thereon. The endoscope imaging unit 47 has the electronic component mounting peninsula portion 75 (example of the circuit mounting peninsula portion) which extends from the flexible substrate 71, which is bent to a side opposite to the image sensor 49 before the image sensor mounting peninsula portion 73, which conductively connects the electronic component 77 or the circuit pattern to the circuit, and which mounts only the electronic component 77 or the circuit pattern thereon. It is preferable that the electronic component mounting peninsula portion 75 is located within the projection area range of the image sensor 49 in a front view when viewed from the front (that is, the front end of the endoscope 11 described above). However, the electronic component mounting peninsula portion 75 may be located so that a portion of the electronic component mounting peninsula portion 75 slightly protrudes to such an extent that interference with other members is minimized.

In the endoscope imaging unit 47 according to Embodiment 1, the flexible substrate 71 is located between the front end of the electric wires 69 and the image sensor 49. The flexible substrate 71 has the circuit including the plurality of linear conductors. The flexible substrate 71 conductively connects the electric wires 69 and the image sensor 49 to each other. The plurality of electronic components 77 are conductively connected to a predetermined circuit, and mounted on the flexible substrate 71. The flexible substrate 71 has the image sensor mounting peninsula portion 73 which is bent parallel to the image sensor 49 and which mounts the image sensor 49 thereon. The flexible substrate 71 is located within the projection area range of the image sensor 49 mounted on the image sensor mounting peninsula portion 73.

The respective electric wires 69 are conductively connected in parallel with the flexible substrate 71. The electric wire 69 has a lower height from the mounting surface than the electronic component 77. The electric wires need to have a predetermined insulation distance from a viewpoint of connection reliability. For example, in the endoscope 11 which needs a thin outer shape in order to maintain low invasiveness to a patient, it is necessary to connect approximately 15 or more of the electric wires 69 in parallel within a length of 3 mm. Therefore, in the endoscope imaging unit 47, the electric wires 69 can be connected using the total length of the edge 103 in the flexible substrate 71. Accordingly, there is no loss in the electric wire connection space since the electronic component 77 is mounted on the edge 103. In the flexible substrate 71, the edge 103 on the side opposite to the image sensor 49 can be used in order to connect all of the electric wires 69. Therefore, a large number of the electric wires 69 can be connected while a predetermined insulation distance is secured. In other words, it is possible to manufacture the flexible substrate 71 in which the edge 103 is minimized in connecting the plurality of predetermined electric wires 69.

On the other hand, the electronic component 77 has a higher mounting height than the electric wire 69. Therefore, the electronic component 77 is mounted on the dedicated electronic component mounting peninsula portion 75 formed separately from the edge 103 to which the electric wire 69 is connected. The electronic component mounting peninsula portion 75 extends from the edge 103 on the image sensor side (side opposite to the electric wire connection side) by being integrated as a portion of the flexible substrate 71, and is bent so as to face the rear surface of the image sensor 49 within the projection area range of the image sensor 49. Accordingly, the electronic component mounting peninsula portion 75 can be located in a columnar three-dimensional space in which a projection area of the image sensor 49 is set to a cross section. That is, the electronic component 77 which needs a housing volume is located so as not to interfere with the electric wire connection space by effectively utilizing the three-dimensional space behind the image sensor.

In this way, the endoscope imaging unit 47 adopts a layout as follows. The electric wire 69 which requires the secured insulation distance with a lower mounting height and the electronic component 77 which requires the housing volume are divided into the mounting surface of the flexible substrate 71 and the dedicated electronic component mounting peninsula portion 75 formed in the flexible substrate 71. In this manner, the outer shape or the volume of the endoscope imaging unit 47 can be minimized by obtaining the connection structure suitable for mounting characteristics of the electric wires 69 and the electronic component 77 within the projection area range of the image sensor 49.

In the endoscope imaging unit 47, the flexible substrate 71 is bent into the tubular body 79 which extends in the same direction as that of the front end straight portion of the electric wire 69. The image sensor mounting peninsula portion 73 extends from the front end peripheral edge portion of the tubular body 79, and is bent in the direction substantially perpendicular to the tubular body 79, i.e., the front end straight portion of the electric wire 69. The electronic component mounting peninsula portion 75 is bent by extending from the other of the front end peripheral edge portion of the tubular body 79, and is inserted into the tubular body 79.

In the endoscope imaging unit 47, the flexible substrate 71 is formed as the tubular body 79. The tubular body 79 fits within the projection area range of the image sensor 49 with the extension of the tubular body 79 oriented in the same direction as that of the front end straight portion of the electric wire 69. Accordingly, the tubular body 79 does not hinder a decrease in the outer diameter of the endoscope 11. The tubular body 79 can be formed so that the outer shape of the cross section perpendicular to the extension direction of the tubular body 79 is set as a circle, an ellipse, or a polygon such as a triangle, a quadrangle, a pentagon, a hexagon, and an octagon.

The flexible substrate 71 is not limited to an example in which the flexible substrate 71 is formed as the tubular body 79 as described above. In a case where a volume for housing the electronic component mounting peninsula portion 75 can be secured, the flexible substrate 71 may be formed as a non-tubular body having a Z-shape, for example. Even in this case, even if the flexible substrate 71 is formed as the non-tubular body, the extension direction is oriented in the same direction as that of the front end straight portion of the electric wire 69. The flexible substrate 71 fits within the projection area range of the image sensor 49, and does not hinder a decrease in the outer diameter of the endoscope 11.

In a case where the flexible substrate 71 is bent to the tubular body 79, the substrate main body 81 can be formed in a spread rectangular shape. In the substrate main body 81, the image sensor mounting peninsula portion 73 and the electronic component mounting peninsula portion 75 are formed to extend on one of a pair of long sides.

In the substrate main body 81, the edge 103 on one long side is the peripheral edge portion of the front end of the tubular body 79 after being bent. In the substrate main body 81, the edge 103 on the other long side is the peripheral edge portion of the rear end of the tubular body on the electric wire withdrawal side after being bent. In the substrate main body 81, the flexible substrate 71 having the image sensor mounting peninsula portion 73 and the electronic component mounting peninsula portion 75 can conductively connect the electric wires 69, the image sensor 49, and the electronic component 77 to each other in a state of a spread flat shape. Therefore, according to the endoscope imaging unit 47, mass production using automation is facilitated.

In the flexible substrate 71, the image sensor 49 and the electronic component 77 are mounted on one surface (outer surface 99 of the tubular body 79) of the image sensor mounting peninsula portion 73 and the electronic component mounting peninsula portion 75 which extend from the substrate main body 81. The plurality of pads 101 conductively connected to the circuit are mounted in advance on the mounting surface of the image sensor mounting peninsula portion 73 and the electronic component mounting peninsula portion 75. The image sensor 49 and the electronic component 77 are mounted by soldering a bump to the pads 101.

In the image sensor mounting peninsula portion 73 and the electronic component mounting peninsula portion 75, the proximal end portion extending from the substrate main body 81 is the constricted portion 95. In the image sensor mounting peninsula portion 73 and the electronic component mounting peninsula portion 75, the constricted portion 95 is bent in the fold 105 parallel to the long side of the substrate main body 81. In addition, both the image sensor mounting peninsula portion 73 and the electronic component mounting peninsula portion 75 may not have the constricted portion 95. In this case, the image sensor mounting peninsula portion 73 is disposed so as to extend from the fourth surface 89 of the flexible substrate 71 while maintaining the same width without being constricted. Similarly, the electronic component mounting peninsula portion 75 is disposed so as to extend from the second surface 85 of the flexible substrate 71 while maintaining the same width without being constricted.

In the flexible substrate 71, the electric wire 69 in the direction along the axis line is connected to the circuit in the substrate main body 81 of the other surface (inner surface 97 of the tubular body 79). For example, in order to connect the electric wires 69 and the circuit to each other, the plurality of pads 101 electrically connected to the linear conductor configuring the circuit are disposed on the inner surface 97 of the substrate main body 81, and the conductor of the electric wire 69 is soldered to the respective pads 101.

In the tubular body 79, the spread flat plate-shaped substrate main body 81 is bent around the axis line so as to form a cylinder or a square tube.

The image sensor mounting peninsula portion 73 and the electronic component mounting peninsula portion 75 protrude forward in the direction from the peripheral edge portion of the front end of the tubular body 79. Out of these, the electronic component mounting peninsula portion 75 is first bent, and is housed inward of the tubular body 79. Thereafter, the image sensor mounting peninsula portion 73 is bent substantially perpendicular to the tubular body 79.

In this way, in the flexible substrate 71 formed as the tubular body 79, the edge 103 is the annular peripheral edge portion, compared to a flat plate shape where the edge 103 is linear. Accordingly, a large parallel installation space of the electric wire 69 can be secured.

In the endoscope imaging unit 47, the electric wire 69 is inserted into the rear end of the tubular body on the side opposite to the image sensor 49, and is conductively connected to the circuit via the pad 101 disposed on the inner surface 97 of the tubular body 79.

In the endoscope imaging unit 47, the plurality of electric wires 69 conductively connected to the inner surface 97 of the tubular body 79 are withdrawn outward by being surrounded by the peripheral edge portion of the rear end of the tubular body. In the tubular body 79, the annular space between the inner peripheral surface and the electronic component mounting peninsula portion 75 is the electric wire withdrawal space. The electronic component 77 is not mounted on the inner surface 97 of the tubular body 79. Accordingly, the electric wire 69 can be withdrawn from the entire inner periphery of the tubular body 79. As a result, compared to a configuration in the related art in which the electronic components 77 are mixed and arranged on the inner surface 97, a large electric wire withdrawal space can be secured.

More specifically, compared to the configuration disclosed in JP-A-2008-237732 (for example, the configuration in FIG. 18 disclosed in JP-A-2008-237732), in the configuration of the endoscope imaging unit 47 according to Embodiment 1, the electronic component 77 is not mounted on the inner surface 97. Accordingly, the electric wire 69 can be withdrawn from the edge 103 (entire inner periphery) of the flexible substrate 71. Then, the central space of the flexible substrate 71 can efficiently house the plurality of electronic components 77 mounted on the bent electronic component mounting peninsula portion 75 (refer to FIG. 4).

In the endoscope imaging unit 47, the tubular body 79 is the square tube.

In the endoscope imaging unit 47, the tubular body 79 is formed in a quadrangular shape. In the spread flat plate-shaped substrate main body 81, at least four folds 105 perpendicular to the long side are set at an equal interval across the pair of parallel long sides. The respective folds 105 are set in the long side portion other than the extending portion of the image sensor mounting peninsula portion 73 and the electronic component mounting peninsula portion 75. The quadrangular tubular body 79 is formed so that the folds 105 are bent at 90 degrees.

The image sensor mounting peninsula portion 73 and the electronic component mounting peninsula portion 75 protrude in the direction from the peripheral edge portion of the front end of the quadrangular tubular body 79. As described above, out of these, the electronic component mounting peninsula portion 75 is first bent, and is housed inward of the tubular body 79. Thereafter, the image sensor mounting peninsula portion 73 is bent substantially perpendicular to the tubular body 79. The plurality of electric wires 69 conductively connected to the inner surface 97 of the tubular body 79 are withdrawn outward by being surrounded by the peripheral edge portion of the rear end of the quadrangular tubular body.

In this way, in the flexible substrate 71 formed as the quadrangular tubular body 79, the edge 103 is the annular peripheral edge portion, compared to the flat plate shape where the edge 103 is linear. Accordingly, a large parallel installation space of the electric wire 69 can be secured. In addition to this advantage, according to the quadrangular tubular body 79, a large housing space having no unnecessary space can be secured in a substantially similar shape within the projection area range of the quadrangular image sensor 49.

The endoscope 11 according to Embodiment 1 has the plurality of parallel electric wires 69 insulated from each other. The endoscope 11 has the image sensor 49 which is located forward (that is, the front end of the endoscope 11 described above) by being separated from the front end of the respective electric wires 69, and in which the light incident surface substantially perpendicular to the front end straight portion of the electric wire 69 faces forward (that is, the front end side of the endoscope 11 described above). The endoscope 11 has the flexible substrate 71 located between the electric wires 69 and the image sensor 49, having a circuit for transmitting the captured image and transmitting a control signal, and conductively connecting the respective electric wires 69 to the circuit. It is preferable that the flexible substrate 71 is located within the projection area range of the image sensor 49 in a front view when viewed from the front (that is, the front end of the endoscope 11 described above). However, the flexible substrate 71 may be located so that a portion of the flexible substrate 71 slightly protrudes to such an extent that interference with other members is minimized. The endoscope 11 has the image sensor mounting peninsula portion 73 which is bent with respect to the fourth surface 89 of the flexible substrate 71, which conductively connects the image sensor 49 to the circuit, and which mounts the image sensor 49 thereon. The endoscope 11 has the electronic component mounting peninsula portion 75 (example of the circuit mounting peninsula portion) which extends from the flexible substrate 71, which is bent to a side opposite to the image sensor 49 before the image sensor mounting peninsula portion 73, which conductively connects the electronic component 77 or the circuit pattern to the circuit, and which mounts only the electronic component 77 or the circuit pattern thereon. The endoscope 11 has the optical unit 39 that forms an image of the light reflected from the object (for example, on the surface or the body interior of the test object) on the light incident surface of the image sensor 49. It is preferable that the electronic component mounting peninsula portion 75 is located within the projection area range of the image sensor 49 in a front view when viewed from the front (that is, the front end of the endoscope 11 described above). However, the electronic component mounting peninsula portion 75 may be located so that a portion of the electronic component mounting peninsula portion 75 slightly protrudes to such an extent that interference with other members is minimized.

The endoscope 11 according to Embodiment 1 includes the endoscope imaging unit 47 and the optical unit 39. In this manner, the outer shape or the volume can be minimized by obtaining the connection structure suitable for the electric wires 69 and the electronic component 77, and furthermore, the outer diameter of the endoscope 11 can be reduced. As a result, compared to the endoscope having the configuration in the related art, observation can be performed by inserting the endoscope 11 into a smaller diameter hole.

The endoscope 11 includes the illumination unit 41 for emitting the illumination light to the object (for example, the surface or the body interior of the test object).

The endoscope 11 includes the endoscope imaging unit 47, the optical unit 39, and the illumination unit 41. Accordingly, compared to the endoscope having the configuration in the related art, independent observation can be performed in a dark place by inserting the endoscope 11 into in a smaller diameter hole.

Next, an endoscope imaging unit 109 according to Embodiment 2 will be described.

Figure 10:
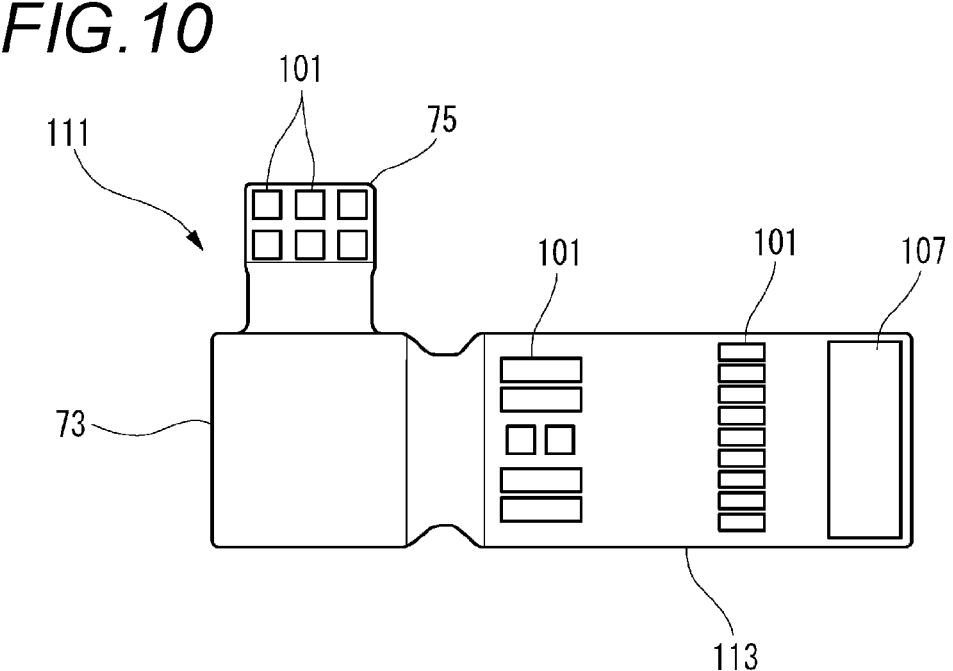
FIG. 10 is a plan view of a flexible substrate according to Embodiment 2.

FIG. 10 is a plan view of a flexible substrate 111 according to Embodiment 2. In Embodiment 2, the same reference numerals will be given to the same configurations as the configurations illustrated in the Embodiment 1, and repeated description thereof will be omitted.

In the endoscope imaging unit 109 according to Embodiment 2, a substrate main body 113 of the flexible substrate 111 is formed in a rectangular plate shape having a side portion whose length is substantially the same as the length of one side of the quadrangular image sensor 49. In the flexible substrate 111, a pair of parallel sides serves as the front and rear edges 103.

The image sensor mounting peninsula portion 73 extends from the edge 103 in the front end of the flexible substrate 111, and is bent parallel to the image sensor 49. The image sensor mounting peninsula portion 73 extends with approximately the same width as that of the substrate main body 113. The electronic component mounting peninsula portion 75 is formed to extend from the image sensor mounting peninsula portion 73. That is, in a spread state, the flexible substrate 111 is formed in an L-shape in which the electronic component mounting peninsula portion 75 extends from the side portion of the image sensor mounting peninsula portion 73.

The plurality of pads 101 conductively connected to the circuit are formed in the width direction at an equal interval in the rear end of the substrate main body 113. In addition, in the endoscope imaging unit 109, the pad 101 for mounting the electronic component 77 is disposed in the front portion of the substrate main body 113. In this case, the substrate main body 113 has no loss in the withdrawal space of the electric wire 69, since all of the rear edges 103 are secured as the withdrawal space of the electric wire 69. In the image sensor mounting peninsula portion 73, the plurality of pads 101 for conductively connecting the circuit to the image sensor 49 are disposed on the rear surface side in FIG. 10. The plurality of pads 101 for mounting the electronic component 77 are disposed in the electronic component mounting peninsula portion 75 formed to extend from the image sensor mounting peninsula portion 73.

Figure 11:
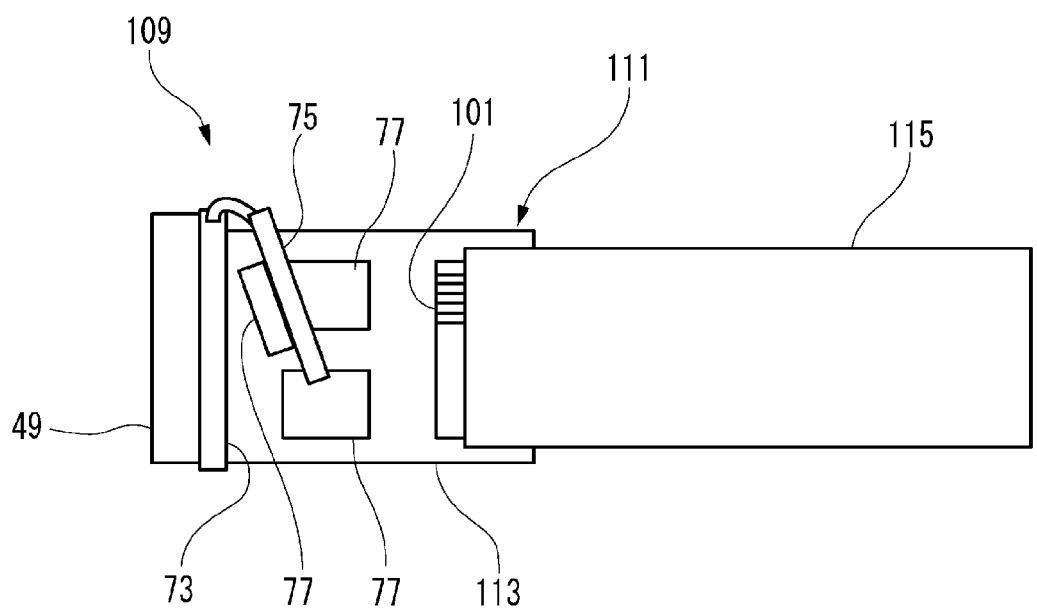
FIG. 11 is a plan view of an endoscope imaging unit employing the flexible substrate illustrated in FIG. 10.

FIG. 11 is a plan view of the endoscope imaging unit 109 employing the flexible substrate 111 illustrated in FIG. 10. In the endoscope imaging unit 109, the plurality of electric wires 69 are formed are respectively formed in an integrated belt-shaped ribbon cable 115. In the flexible substrate 111, in a spread state having a flat plate shape, the respective electric wires 69 in the front end of the ribbon cable 115 are conductively connected to the circuit in the rear edge 103. The connected ribbon cable 115 is withdrawn from the rear edge 103 of the flexible substrate 111. The electronic component 77 is mounted on the pad 101 in the front portion of the substrate main body 113. The image sensor 49 is mounted on the image sensor mounting peninsula portion 73. The electronic component 77 is mounted on the electronic component mounting peninsula portion 75.

FIG. 12 is a side view of the endoscope imaging unit illustrated in FIG. 11. The flexible substrate 111 is bent in the fold 105 along the edge 103 so that the image sensor mounting peninsula portion 73 is erected from the substrate main body 113. In addition, the electronic component mounting peninsula portion 75 is bent in the fold 105 along one side of the quadrangular image sensor mounting peninsula portion 73, and is located to face to face on the rear surface side with respect to the image sensor mounting peninsula portion 73. If the substrate main body 113 and the ribbon cable 115 are arranged within the projection area range of the image sensor 49, wiring can be performed in a freely bent shape.

Next, an operation of the endoscope imaging unit 109 according to Embodiment 2 will be described.

In the endoscope imaging unit 109, the plurality of respective electric wires 69 are formed in in the integrated belt-shaped ribbon cable 115. In the flexible substrate 111, the respective electric wires 69 are conductively connected to the circuit in the front end of the ribbon cable 115. The image sensor mounting peninsula portion 73 extends from the edge 103 of the flexible substrate 71 on the side opposite to the ribbon cable 115, and is bent parallel to the image sensor 49. The electronic component mounting peninsula portion 75 is formed to extend from the image sensor mounting peninsula portion 73.

In the endoscope imaging unit 109, the substrate main body 113 of the flexible substrate 111 is used in a flat plate without any change. The image sensor mounting peninsula portion 73 extending to the substrate main body 113 is formed by further extending the electronic component mounting peninsula portion 75. In this manner, the endoscope imaging unit 109 can house the ribbon cable 115 and the electronic component 77 within the projection area range of the image sensor 49 by using a simpler structure instead of forming the tubular body.

Therefore, according to the endoscope imaging unit 47 and 109 in Embodiments 1 and 2, the outer shape or the volume can be minimized by obtaining the connection structure suitable for the electric wires 69 and the electronic component 77 within the projection area range of the image sensor 49 in a front view when viewed from the front (that is, the front end of the endoscope 11 described above).

According to the endoscope 11 in Embodiment 1 and the endoscope 11 in Embodiment 2, the outer shape or the volume can be minimized by obtaining the connection structure suitable for the electric wires 69 and the electronic component 77 within the projection area range of the image sensor 49 in a front view when viewed from the front (that is, the front end of the endoscope 11 described above), and the outer diameter of the endoscope 11 can be reduced.

Hitherto, various embodiments have been described with reference to the drawings. However, as a matter of course, the present disclosure is not limited to the examples. It is obvious that various modifications, corrections, substitutions, additions, deletions, and equivalents within the scope disclosed in the appended claims are conceivable by those skilled in the art. It should be naturally understood that all of these belong to the technical scope of the present disclosure. In addition, the respective configuration elements in the various embodiments described above may be optionally combined with each other within the scope not departing from the gist of the invention.

The present disclosure is useful for the endoscope imaging unit and the endoscope in which the outer shape or the volume can be minimized by obtaining the connection structure suitable for the electric wires and the electronic component within the projection area range of the image sensor 49 in a front view when viewed from the front, and in which the outer diameter can be reduced.

This application is based upon and claims the benefit of priorities of Japanese Patent Applications No. 2018-135094 filed on Jul. 18, 2018, the contents of which are incorporated herein by reference in its entirety.

The reference numerals and signs used in the present disclosure are listed below.

11: endoscope
39: optical unit
41: illumination unit
47: endoscope imaging unit
49: image sensor
69: electric wire
71: flexible substrate
73 image sensor mounting peninsula portion
75: electronic component mounting peninsula portion
77: electronic component
79: tubular body
97: inner surface
101: pad
103: edge
109: endoscope imaging unit
111: flexible substrate
115: ribbon cable

What is claimed is:

1. An endoscope imaging unit comprising:
a plurality of parallel electric wires insulated from each other and extending in a first direction;
an image sensor located at a front end side of the endoscope imaging unit, the image sensor being separated from front ends of the plurality of parallel electric wires, the image sensor having a light incident surface extending in a second direction substantially perpendicular to the first direction and facing the front end side;
a flexible substrate located between the plurality of parallel electric wires and the image sensor, the flexible substrate including:
a circuit in the flexible substrate and conductively connected to the plurality of parallel electric wires;
a first surface;
a second surface opposite to the first surface;
a main body portion having a plurality of folds such that first and second portions of the first surface face each other and third and fourth portions of the first surface face each other, the plurality of parallel electric wires being on the first, second, third, and fourth portions of the first surface, the main body portion being folded into a tubular body to surround portions of the plurality of parallel electric wires;
an image sensor mounting peninsula portion bent with respect to the main body portion and extending from the main body portion in the second direction, the image sensor mounting peninsula portion extending from a first peripheral edge portion of the tubular body, the image sensor being on the image sensor mounting peninsula portion and the second surface, the image sensor being conductively connected to the circuit; and
a circuit mounting peninsula portion bent with respect to the main body portion and extending from the main body portion,
the circuit mounting peninsula portion extending from a second peripheral edge portion of the tubular body,
the circuit mounting peninsula portion being bent such that a portion of the circuit mounting peninsula portion is inserted into an opening of the tubular body, the portion of the circuit mounting peninsula portion is spaced from the first, second, third, and fourth portions of the first surface, and the first, second, third, and fourth portions of the first surface are spaced from each other by the portion of the circuit mounting peninsula portion,
at least a portion of the circuit mounting peninsula portion being spaced from the image sensor in the first direction by the image sensor mounting peninsula portion, and positioned between the main body portion and the image sensor mounting peninsula portion in the first direction,
the circuit mounting peninsula portion being connected to the image sensor mounting peninsula portion by the main body portion, and positioned on the same side of the main body portion as the image sensor mounting peninsula portion; and
an electronic component or a circuit pattern on the circuit mounting peninsula portion and the second surface of the main body portion, the electronic component or the circuit pattern being conductively connected to the circuit.

2. The endoscope imaging unit according to claim 1, wherein the flexible substrate is located within a projection area range of the image sensor when viewed from the front end side, and
wherein the circuit mounting peninsula portion is located within the projection area range of the image sensor.

3. The endoscope imaging unit according to claim 1, wherein the plurality of parallel electric wires are inserted into a rear end side of the tubular body on a side opposite to the image sensor, and is conductively connected to the circuit via a pad disposed on an inner surface of the tubular body.

4. The endoscope imaging unit according to claim 1, wherein the tubular body is a square tube.

5. The endoscope imaging unit according to claim 2, wherein the plurality of parallel electric wires are respectively formed in an integrated belt-shaped ribbon cable,
wherein the flexible substrate is connected to a front end of the ribbon cable by conductively connecting the plurality of parallel electric wires to the circuit,
wherein the image sensor mounting peninsula portion extends from an edge of the flexible substrate on a side opposite to the ribbon cable, and is bent parallel to the image sensor, and
wherein the circuit mounting peninsula portion is formed by extending from the image sensor mounting peninsula portion.

6. An endoscope comprising:
a plurality of parallel electric wires insulated from each other and extending in a first direction;
an image sensor located at a front end side of the endoscope, the image sensor being separated from front ends of the plurality of parallel electric wires, the image sensor having a light incident surface extending in a second direction substantially perpendicular to the first direction and facing the front end side;
a flexible substrate located between the plurality of parallel electric wires and the image sensor, the flexible substrate including:
a circuit in the flexible substrate and conductively connected to the plurality of parallel electric wires;
a first surface;
a second surface opposite to the first surface;
a main body portion having a plurality of folds such that first and second portions of the first surface face each other and third and fourth portions of the first surface face each other, the plurality of parallel electric wires being on the first, second, third, and fourth portions of the first surface, the main body portion being folded into a tubular body to surround portions of the plurality of parallel electric wires;
an image sensor mounting peninsula portion bent with respect to the main body portion and extending from the main body portion in the second direction, the image sensor mounting peninsula portion extending from a first peripheral edge portion of the tubular body, the image sensor being on the image sensor mounting peninsula portion and the second surface, the image sensor being conductively connected to the circuit;
a circuit mounting peninsula portion bent with respect to the main body portion and extending from the main body portion,
the circuit mounting peninsula portion extending from a second peripheral edge portion of the tubular body,
the circuit mounting peninsula portion being bent such that a portion of the circuit mounting peninsula portion is inserted into an opening of the tubular body, the portion of the circuit mounting peninsula portion is spaced from the first, second, third, and fourth portions of the first surface, and the first, second, third, and fourth portions of the first surface are spaced from each other by the portion of the circuit mounting peninsula portion,
at least a portion of the circuit mounting peninsula portion being spaced from the image sensor in the first direction by the image sensor mounting peninsula portion, and positioned between the main body portion and the image sensor mounting peninsula portion in the first direction,
the circuit mounting peninsula portion being connected to the image sensor mounting peninsula portion by the main body portion, and positioned on the same side of the main body portion as the image sensor mounting peninsula portion; and
an electronic component or a circuit pattern on the circuit mounting peninsula portion and the second surface of the main body portion, the electronic component or the circuit pattern being conductively connected to the circuit; and
an optical lens configured to cause light reflected from an object to form an image on the light incident surface.

7. The endoscope according to claim 6, further comprising:
an emitter configured to emit illumination light to the object.

8. The endoscope imaging unit according to claim 1, wherein the image sensor mounting peninsula portion and the circuit mounting peninsula portion are aligned with an opening of the tubular body.

9. The endoscope imaging unit according to claim 8, wherein a portion of the main body portion extends into the tubular body.

10. The endoscope imaging unit according to claim 1, wherein a respective set of wires of the plurality of parallel electric wires is positioned on each of the first, second, third, and fourth, portions of the first surface.

11. The endoscope imaging unit according to claim 1, wherein the first peripheral edge portion and the second peripheral edge portion are on opposite sides of the tubular body.

12. The endoscope imaging unit according to claim 1, wherein the main body portion is folded such that an end portion of the main body portion extends into the tubular body.

13. The endoscope imaging unit according to claim 12, wherein the end portion of main body portion extends from a first side of the tubular body to a second side, opposite to the first side, of the tubular body, and contactable with the second side of the tubular body.

* * * * *